US00PP23863P2

(12) United States Plant Patent
Ronald

(10) Patent No.: US PP23,863 P2
(45) Date of Patent: Sep. 3, 2013

(54) ***MALUS* TREE NAMED 'JEFGREEN'**

(50) Latin Name: *Malus×adstringens*
Varietal Denomination: Jefgreen

(76) Inventor: Wilbert G. Ronald, Portage la Prairie (CA)

( * ) Notice: Subject to any disclaimer, the term of this patent is extended or adjusted under 35 U.S.C. 154(b) by 165 days.

(21) Appl. No.: 13/199,410

(22) Filed: Aug. 29, 2011

(51) Int. Cl.
*A01H 5/00* (2006.01)

(52) U.S. Cl.
USPC ..... Plt./173

(58) Field of Classification Search
USPC ..... Plt./173
See application file for complete search history.

*Primary Examiner* — Kent L Bell
(74) *Attorney, Agent, or Firm* — Penny J. Aguirre

(57) ABSTRACT

A new and distinctive cultivar of flowering crabapple, botanically known as *Malus* 'Jefgreen', that is characterized by its columnar plant habit, its foliage that is bronze-green in color in spring that change to green in color in summer, its light pink flowers opening from pink flower buds, its cold hardiness at least in U.S.D.A. Zone 3, and its good resistance to apple scab and fireblight.

2 Drawing Sheets

Botanical classification: *Malus×adstringens*.
Variety denomination: 'Jefgreen'.

BACKGROUND OF THE INVENTION

The present invention relates to a new and distinct cultivar of *Malus×adstringens* and will be referred to hereafter by its cultivar name, 'Jefgreen'. 'Jefgreen' is a deciduous tree grown for use as an ornamental landscape plant.

The new *Malus* arose from a breeding program conducted by the Inventor at a nursery in Portage la Prairie, Manitoba, Canada. The objective of the breeding program was to develop new cultivars of *Malus* with unique characteristics in combination with columnar plant habits and improved vigor and cold hardiness.

The new *Malus* originated from an open pollination of an unnamed *Malus* tree, breeders code name T4, in spring of 2003. 'Jefgreen' was selected as a unique single plant from the progeny derived from the open pollination in spring of 2006. The male parent is thought to be *Malus* 'Selkirk' (not patented) based on the characteristics of 'Jefgreen' and its proximity to the female parent.

Asexual reproduction of the new cultivar was first accomplished by budding in Portage la Prairie, Manitoba, Canada by the Inventor in summer of 2006. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Jefgreen' as a unique cultivar of *Malus*.

1. 'Jefgreen' exhibits a columnar plant habit.
2. 'Jefgreen' exhibits foliage that is bronze-green in color in spring and becoming green in color in summer.
3. 'Jefgreen' exhibits light pink flowers opening from pink flower buds.
4. 'Jefgreen' exhibits cold hardiness at least in U.S.D.A. Zone 3.

5. 'Jefgreen' exhibits good resistance to apple scab and fireblight.

The new cultivar can be compared to its female parent plant, code name T4, which differs from 'Jefgreen' in having purple foliage in summer, a different leaf shape, and less hardiness, vigor and fruit production. 'Jefgreen' can also be compared to its likely male parent, 'Selkirk', which differs from 'Jefgreen' in lacking a columnar plant habit and in producing more flowers. 'Jefgreen' can also be compared to 'Jefspire' (not patented). 'Jefspire' is similar to 'Jefgreen' in having a columnar plant habit but differs from 'Jefgreen' in having less plant vigor, less cold hardiness, less flowers and fruit, and in having foliage that is purple in color in summer.

BRIEF DESCRIPTION OF THE DRAWING

The accompanying colored photographs illustrate the overall appearance and distinct characteristics of the new *Malus* as grown in Portage la Prairie, Manitoba, Canada. The plants in the photograph are about 4 years in age with 'Jefgreen' budded onto *Malus* rootstock.

The photograph in FIG. 1 provides a view of the plant habit and foliage color in Spring of 'Jefgreen'.

Figure 1:
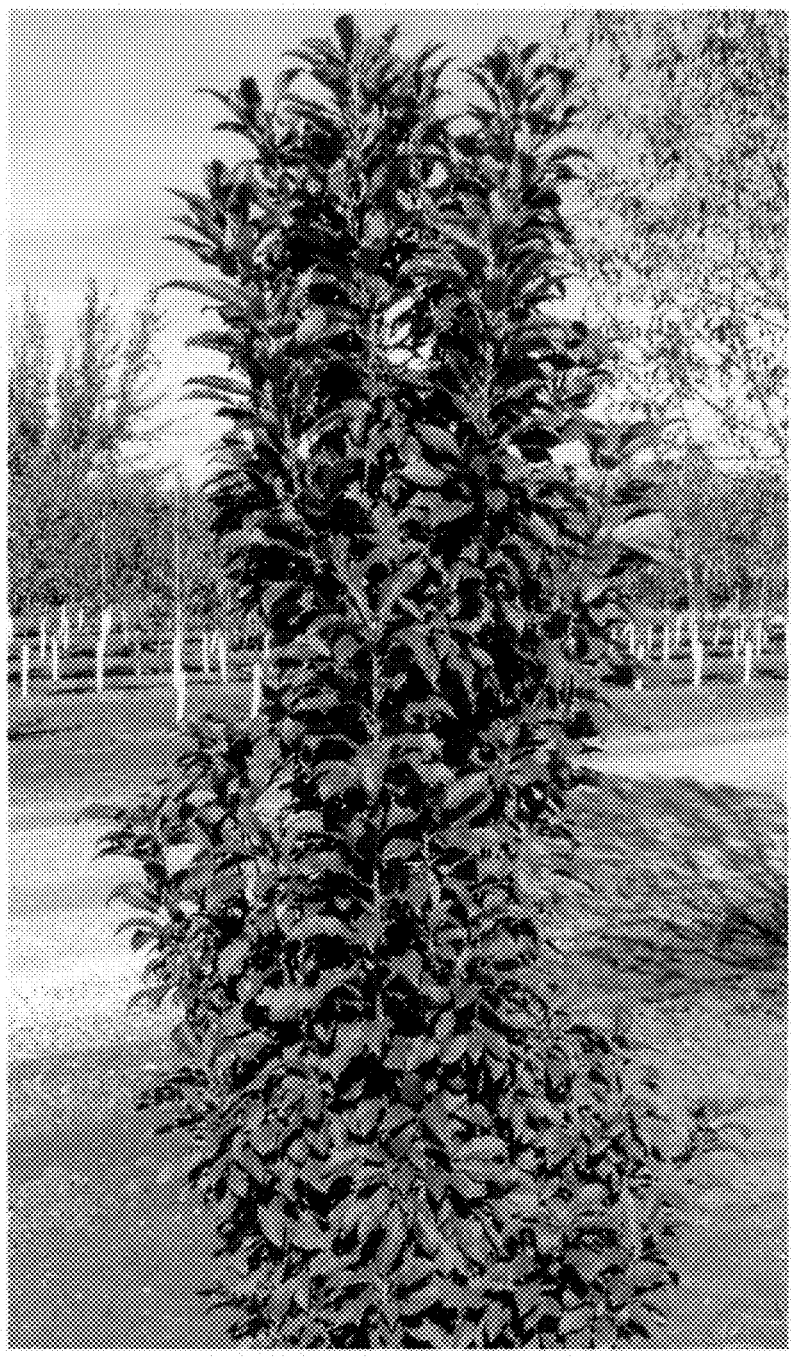
Figure 2:
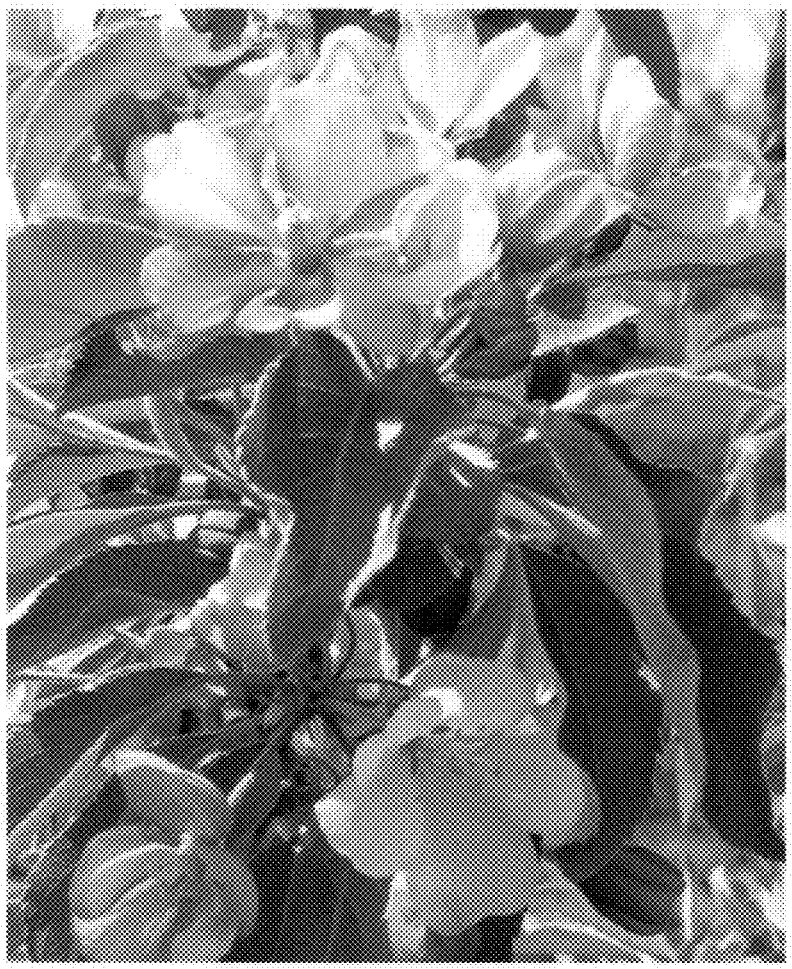

The photograph in FIG. 2 provides a close-up view of the flowers of 'Jefgreen'.

Figure 3:
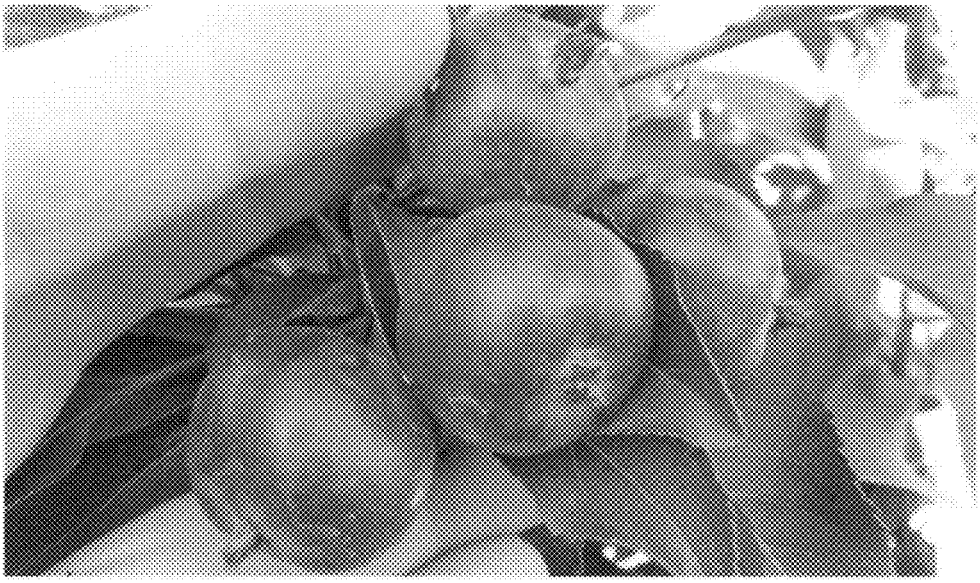

The photograph in FIG. 3 provides a close-up view of the fruit of 'Jefgreen'.

The colors in the photographs are as close as possible with the digital photography techniques available, the color values cited in the detailed botanical description accurately describe the colors of the new *Malus*.

DETAILED BOTANICAL DESCRIPTION

The following is a detailed description of four year-old trees of 'Jefgreen' budded onto *Malus* rootstock and grown in a trial plot in Portage la Prairie, Manitoba, Canada. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

Tree description:

*Tree habit.*—Columnar.

*Height and spread.*—Average of 9 ft in height and 2 ft in diameter at 4 years of age.

*Diseases and pests.*—Good resistance to apple scab and fireblight, no viruses found to date.

*Cold hardiness.*—At least in U.S.D.A. Zone 3.

*Propagation.*—Budding onto *Malus* rootstock.

*Growth rate.*—Moderate.

*Trunk.*—About 1.5 inches in width (measured at 3 inches from budding point), bark is 166A in color with lenticels; about 20 per 7 sq cm, 163D in color, about 5 mm in length and 2 mm in width.

Branches:

*Branching habit.*—An average of 9 branches, strong, upright branches held at an angle of about 60° to the main stem.

*Branch internode length.*—7 to 12 inches.

*Branch angle.*—Upright at 60°.

*Branch shape.*—Round.

*Branch strength.*—Strong.

*Branch size.*—An average of 22.22 inches in length and 0.5 to 0.75 inches in width.

*Branch surface.*—Pubescent (abundant on new growth).

*Bark surface.*—Smooth with lenticels.

*Branch color.*—Mature 200A, new growth 187A.

*Lenticels.*—About 25 between nodes, about 5 mm in length and 1.5 mm in width, 163C in color.

Leaf description:

*Leaf orientation.*—Horizontal.

*Leaf division.*—Simple.

*Leaf shape.*—Elliptic.

*Leaf size.*—Average of 10.07 inches in length and 4.97 inches in width.

*Leaf apex.*—Acuminate.

*Leaf base.*—Cuneate to oblique.

*Leaf surface.*—Glossy on upper surface and pubescent on lower surface.

*Leaf margin.*—Serrate.

*Leaf internode length.*—Average of 2 inches.

*Leaf color.*—Young upper surface; 183A, young lower surface; 182B, mature upper surface; 147A, mature lower surface; 147C, fall color upper and lower surface; 166A.

*Leaf venation.*—Pinnate, average of 12 pairs, color upper and lower surface 191D.

*Petioles.*—Average of 3.4 inches in length and ⅛ inches in diameter, pubescent surface, 187A in color.

*Stipules.*—147A in color, an average of ⅜ inches in length and width, glossy surface.

Flower description:

*Flowering period.*—2 weeks in mid May in Manitoba, early flowering.

*Lastingness of flowers.*—About 10 days.

*Number of flowers.*—Average of 5 per corymb.

*Inflorescence type.*—Corymb of rotate flowers.

*Inflorescence size* (*corymb*).—An average of 4 inches in length and 6 inches in width.

*Flower buds.*—60D in color prior to opening, round in shape, average of 1.8 inches in length and 1 inch in diameter.

*Flower size.*—Average of 2.75 inches in diameter and 1.8 inches in depth.

*Flower quantity.*—Average of 5 per axillary node.

*Flower fragrance.*—Strong.

*Flower aspect.*—Outward.

*Petals.*—5 per flower, un-fused, slightly overlapping, obovate in shape, obtuse apex, round base, entire margin, about 1.3 inches in length and 0.7 inches in width, color upper and lower surface when opening: a blend of 60D and 62C, color upper and lower surface when mature: slightly lighter than 60D, upper and lower surface is smooth and satiny.

*Sepals.*—5 per flower, 191B in color with tips flushed with 178B on upper and lower surface, pubescence surface, tips triangular in shape, entire margin, acuminate apex, base fused into tube, average of 1 inch in length and 0.75 inches in width with tube portion about 0.5 inches in length and width.

*Pedicel.*—178D in color, average of 2 inches in length and ⅛ inch in width, surface is pubescent.

*Pistil.*—Compound carpel with 3 stigmas fused at base, about 0.5 inches in length, style is 145D in color, stigma is very small, ovary is pubescent and 60D in color.

*Stamens.*—About 16 per flower, anther is oblong in shape, 145C in color, filament about 1 inch in length and 155A in color, pollen was not observed.

Fruit description:

*Shape.*—Round.

*Size.*—Average of 1⅛ inches in diameter.

*Skin.*—Smooth surface with glaucous coating, 59C in color.

*Flesh color.*—About 158D.

*Fruit presence.*—In June in Manitoba, Canada.

*Seed.*—Nearly renal-shaped, 4 to 5 per fruit, 1 per chamber, about 5 mm in length and 2 mm in width, 200A in color.

It is claimed:

1. A new and distinct cultivar of *Malus* tree named 'Jefgreen' as herein illustrated and described.

* * * * *